United States Patent [19]

Clarke et al.

[11] Patent Number: 5,061,026
[45] Date of Patent: Oct. 29, 1991

[54] LIGHT ROD ASSEMBLY FOR SPARK DETECTION SYSTEM

[75] Inventors: W. James Clarke; Kris J. Newman, both of Eugene, Oreg.

[73] Assignee: Clarke's Sheet Metal, Inc., Eugene, Oreg.

[21] Appl. No.: 572,904

[22] Filed: Aug. 23, 1990

[51] Int. Cl.$^5$ .......................... G02B 6/00; G02B 6/14
[52] U.S. Cl. ....................................... 385/31; 385/147
[58] Field of Search ................ 350/96.10, 96.15, 96.20

[56] References Cited

U.S. PATENT DOCUMENTS 4,750,795 6/1988 Blotekjaer ........................ 350/96.10
4,784,456 11/1988 Smith ................................ 350/96.10

Primary Examiner—William L. Sikes
Assistant Examiner—Robert E. Wise
Attorney, Agent, or Firm—Chernoff, Vilhauser, McClung & Stenzel

[57] ABSTRACT

A readily replaceable light rod assembly for coupling infrared energy to a photoelectric sensor element in a spark detector system used for monitoring a zone through which fine particulate matter is conveyed at high speed by pneumatic action. The light rod assembly comprises an elongate clad glass rod of optical glass, polished at both ends, positioned inside a tubular housing of Teflon material. The glass rod is fastened inside the housing by a set screw and both ends of the housing are threaded, with the input, or high thermal energy end, screwing into an end cap holding a quartz glass window, and the other, or output end, into the threaded receptacle of the sensor element.

10 Claims, 3 Drawing Sheets

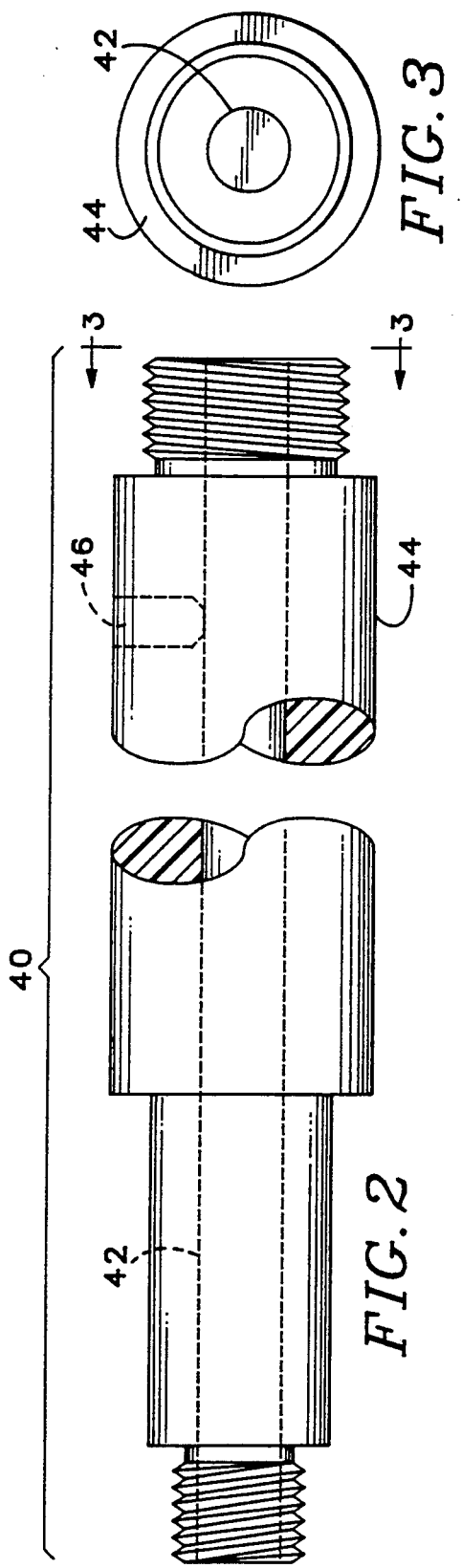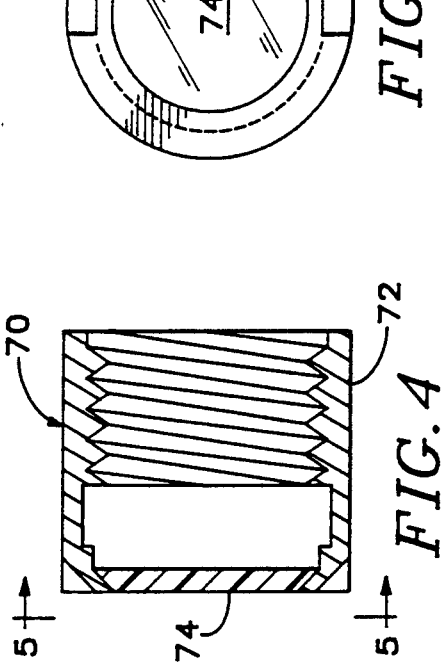

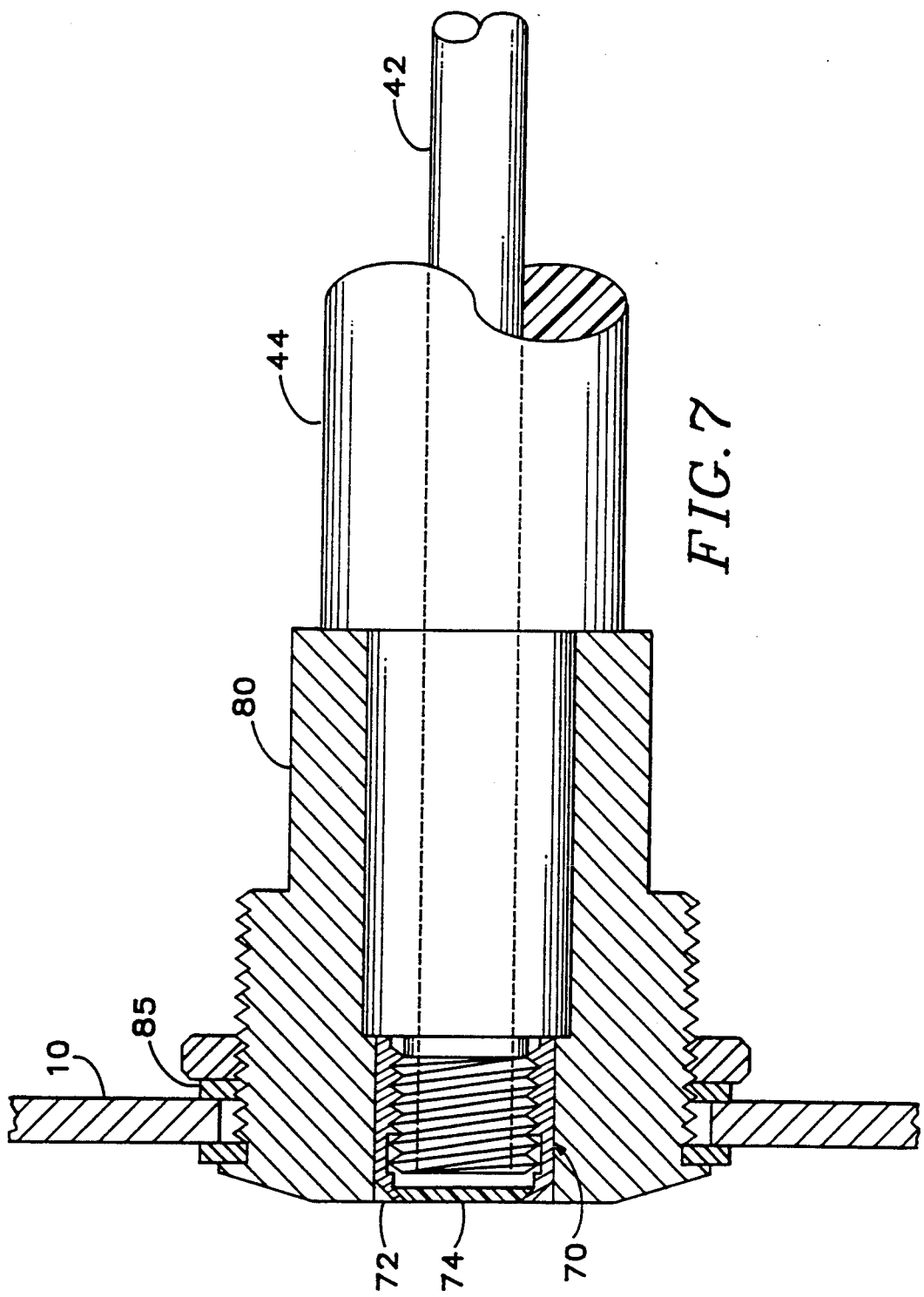

LIGHT ROD ASSEMBLY FOR SPARK DETECTION SYSTEM

BACKGROUND OF THE INVENTION

This invention relates to improvements in the phototransmission portion of a spark detector system and, more particularly, is directed to a readily replaceable light rod assembly for coupling infrared energy to a photoelectric sensor element in such a system.

Conventional spark detection and extinguishing systems, such as those sold in this country by Clarke's Sheet Metal, Inc. (the assignee of applicants) and Fagus-Grecon, Greten GmbH and Co. KG, utilize a fiber optic "polyp," consisting of fiber optic bundles joined together as a trunk at one end to form a single output and divided at the other end into a plurality (typically, three) of limbs which serve as inputs, or photo energy gatherers, for coupling photoelectric energy, such as the thermal energy generated by a spark in a zone or region being monitored, to a sensor element for converting that energy into an electrical signal for processing by the spark detection and extinguishing system.

Conventionally, three input fiber optic bundles, coupling to a single output and spacedly arranged in a circular configuration around the periphery of a zone, are required to effectively monitor a region. A typical application for such systems is in flow pipes and conduits, referred to hereinafter as ducts, through which fine particulate matter such as wood particles or grain are conveyed at high speed by pneumatic action. In such applications the appearance of a spark, caused for example by a foreign body frictionally rubbing against the interior surfaces of the conduit, if not rapidly detected and quickly extinguished, can lead to an explosion and/or fire, with destructive consequences. Thus, systems of the type referred to above have been developed to monitor for the presence of sparks in one or more zones through which the particulate matter flows and then, when a spark is sensed, to actuate appropriate mechanisms, such as water spray valves, to extinguish the spark and also to sound alarms.

As noted, the aforementioned polyps are used as a pick-up or input device for coupling the thermal energy in the infrared and near infrared light spectrum developed by a spark to a photoelectric sensor element that converts the detected energy into an electrical signal. However, these polyp devices have certain disadvantages that limit their effectiveness, as well as the ease and cost of their maintenance and repair. For example, one of the principal disadvantages of the conventional polyp configuration of fiber optic bundles is that, if any one leg of the polyp is damaged, the unit must be replaced in its entirety. In addition to the cost involved, the replacement of a polyp unit is relatively time consuming and labor intensive, since the input or limb ends, with typically three being required to effectively cover a monitoring zone, must each be individually removed, and then the limbs of a replacement polyp installed at each location in place of the removed limb.

Another disadvantage of the conventional polyp assembly is that, as previously mentioned, three are required to effectively cover a single zone, since the viewing angle of an individual fiber optic limb is only about 65°.

SUMMARY OF THE PRESENT INVENTION

The present invention is directed to an improved device, in the form of a replaceable light rod assembly, for monitoring a zone under observation and coupling the thermal energy of a detected spark passing through the zone to a photoelectric sensor, the typical application being in a spark detection and extinguishing system of the type described. In the present invention, in place of the conventional fiber optic polyp, a light rod assembly is employed. In addition to the inherent advantages in performance of a light rod as contrasted to a fiber optic bundle of corresponding size and length, namely, much higher sensitivity and lower cost, the light rod assembly is readily replaced in the event of breakage or other failure, and this can be accomplished without requiring access to the other light rod assemblies monitoring other portions of the same zone.

It is therefore a principal objective of the present invention to provide, in a spark detection and extinguishing system, an improved means for coupling photo energy generated by a spark passing through a zone under observation to a photosensor element for converting the thermal energy of the detected spark into an electrical signal.

It is a further objective of the present invention to provide a coupling device of the type described which is more advantageous in use in regard to initial cost, range of viewing angle effectiveness, and replacement, than the fiber optic polyps conventionally used for this purpose.

It is a principal feature of the present invention to utilize a light rod assembly, which is readily replaceable in the event of failure, as the means for coupling the thermal energy of a detected spark to a photoelectric sensor element.

The foregoing and other objectives, features, and advantages of the present invention will be more readily understood upon consideration of the following detailed description of the invention, taken in conjunction with the accompanying drawings.

BRIEF DESCRIPTION OF THE DRAWINGS

FIG. 2 is a foreshortened plan view showing details of an embodiment of the light rod assembly of the present invention.

FIG. 3 is an end view, taken along the line 3—3, of the 1 assembly depicted in FIG. 2.

FIG. 4 is a cross-sectional axial view of an end cap, comprising a holder and a quartz glass window, which fastens to the input, or energy-gathering end, of the light rod assembly.

FIG. 5 is an end view, taken along the line 5—5, of the end cap depicted in FIG. 4.

FIG. 6 is a top plan view of the guide clamp which serves to hold the light rod assembly in place.

FIG. 7 is a sectional view showing an assembled portion of the light rod assembly as mounted in a conveyor duct.

DETAILED DESCRIPTION OF THE INVENTION

Figure 1:
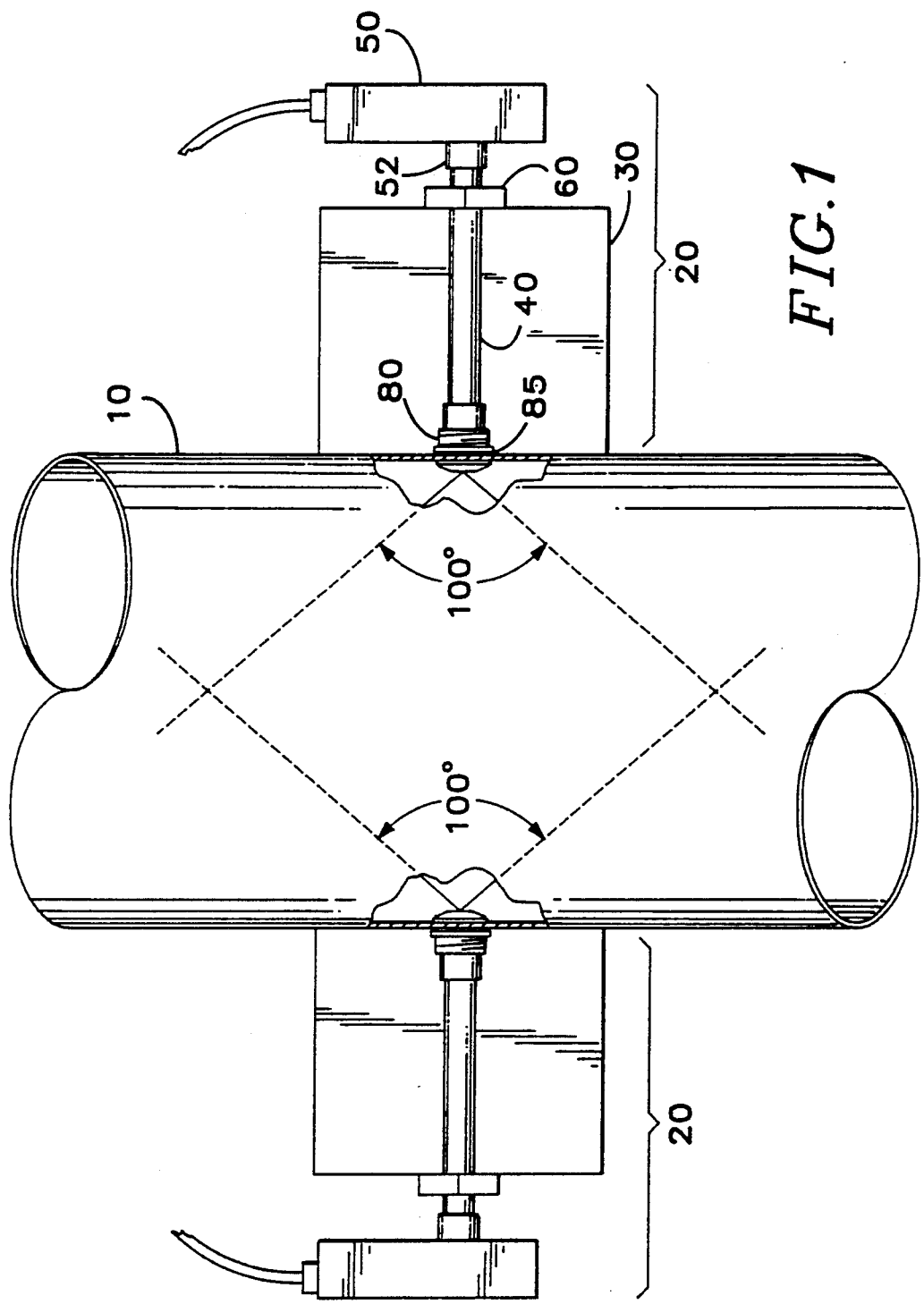
FIG. 1 is a partially sectional plan view showing a pair of spark detection sensors respectively connected to light rod assemblies of the present invention which are mounted so as to a monitor a zone of a conveyor duct.

Referring to FIG. 1, a conveyor duct 10 is shown through which particulate material such as sawdust passes at high speed under the force of a blower or other pneumatic device. Diametrically arranged on the periphery of the duct 10 are a pair of devices, each designated generally as 20, for monitoring a zone of the duct to detect the presence of a spark therein. Each of the devices includes a U-shaped mounting bracket 30 for holding a light rod assembly 40 and a sensor element 50 coupled thereto. (Because of the 100° viewing angle of the light rod assembly 40 it is possible to effectively monitor a duct zone using just two of the units, in contrast to the three fiber optic limbs of a conventional trifurcated polyp which have approximately only a 65° viewing angle.)

The sensor unit 50, which is coupled to the light rod assembly 40 by guide clamp 60, is conventional and may for example be of the type sold by Clarke's under the part designation 7001-00200 or by Fagus-Grecon under the part designation FM 3/6. It forms no part of the present invention. As shown in FIG. 6, the guide clamp 60 is in the form of a split-yoke rectangular plate with a circular opening 65, with one portion thereof 62 fixedly fastened to the mounting bracket 30 by screws 66a, 66b, and the other portion 64 fastened thereto by a pair of lag bolts 68a, 68b.

As shown in FIGS. 2 and 3, the light rod assembly 40 comprises an elongate clad glass rod 42 positioned inside a tubular housing 44 of Teflon material. The rod 42 is of optical glass, polished at both ends, and forms a rigid light guide with an approximately 100° viewing angle. The optical transmission characteristics for a rod of 8.75 inches in length and 0.313 inches in diameter are preferably on the order of 69% at 450 nanometers (infrared) and 87% at 700 nanometers (near infrared) respectively. The glass rod 42 is fastened inside the housing 44 by a set screw 46. Both ends of the housing are threaded, with the input, or high thermal energy end, screwing into an end cap 70 (shown in FIGS. 4 and 5) holding a quartz glass window, and the other, or output end, screwing into the threaded receptacle 52 of the sensor element 50.

The end cap 70 is comprised of a squat tubular holder 72 of stainless steel into which is recessed and fastened by adhesive a quartz glass window or wafer element 74. The end cap in turn slideably fits into the interior opening of a tubular mounting adapter 80 which is externally threaded so that it may be securely installed by a nut-and-washer combination 85 in an opening formed in the wall of the duct 10. FIG. 7 shows the aforementioned elements 42, 44, 70, 72 and 74 as assembled together and installed in the duct wall opening. It will be noted that a small air gap may exist between the quartz window 74 and the end of the glass rod 42.

In the event of need for replacement of the light rod assembly 50, due to breakage or the like, the lag bolts 68a, 68b on the split-yoke of the guide clamp assembly 60 are loosened, allowing the light rod assembly 40 in its entirety to be slideably uncoupled from the mounting adapter 80. After the light rod is slid out of the guide clamp 60, it is then unscrewed from the receptacle 52 of the sensor unit 50, a replacement light rod assembly reinserted therein and the unit reinstalled by the reversal of the aforementioned procedure.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed:

1. A light rod assembly for coupling photo energy detected in a zone of interest, defined at least in part by a wall member, to a photosensor device converting such energy into an electrical signal, said assembly comprising an elongate rigid rod having optical transmission characteristics in the infrared spectrum, a pane of quartz glass optically coupled to one end of said rod, said photosensor device being coupled to the other end thereof, and means adapted to be mounted to said wall member proximate an opening therein, said means removably holding said rod and said pane in fixed positions relative to each other and to said zone.

2. A light rod assembly according to claim 1 wherein said zone lies within a duct through which material is conveyed and said means is adapted to be connected thereto.

3. A light rod assembly according to claim 1 wherein said means includes a detachable clamp grippingly holding said rod by applying radial pressure thereto.

4. A light rod assembly according to claim 3 wherein said zone lies within a duct through which material is conveyed and said means is adapted to be connected thereto.

5. A light rod assembly according to claim 3 wherein said clamp is in the form of a split-yoke plate, said plate being comprised of a pair of elements which, when closed together, form a generally circular opening therein.

6. A light rod assembly according to claim 1 wherein said rod is housed within a tubular sleeve, and means are provided for fixedly securing said rod within said sleeve.

7. A light rod assembly according to claim 1 further including a cap connected to an end of said rod for holding said pane in optically coupled relationship therewith.

8. A light rod assembly according to claim 1 wherein said means includes a detachable clamp grippingly holding said rod and a mounting bracket of general U-shaped configuration connecting said clamp to a portion of said duct.

9. A light rod assembly for coupling photo energy to a photosensor device converting such energy into an electrical signal, said assembly comprising an elongate rigid rod having optical transmission characteristics in the infrared spectrum, a substantially circular pane of quartz glass, a round end cap holding said pane, and a tubular sleeve within which said rod is housed, said sleeve being threaded at an end thereof for removably engaging said cap so as to maintain said pane and said rod in optically coupled relationship.

10. A light rod assembly according to claim 9 wherein the other end of said sleeve is threaded for removably engaging said photosensor device.

* * * * *

UNITED STATES PATENT AND TRADEMARK OFFICE
CERTIFICATE OF CORRECTION

PATENT NO.  : 5,061,026
DATED       : October 29, 1991
INVENTOR(S) : W. James Clarke et al.

It is certified that error appears in the above-identified patent and that said Letters Patent is hereby corrected as shown below:

Column 2, line 50, after "so as to" delete "a".

Column 2, line 56, (FIG. 3 description), delete "1" insert -- light rod--.

Signed and Sealed this

First Day of February, 1994

Attest:

BRUCE LEHMAN

*Attesting Officer*   *Commissioner of Patents and Trademarks*